United States Patent [19]

Jolly

[11] Plant 4,849

[45] May 25, 1982

[54] ROSE PLANT

[76] Inventor: Betty J. Jolly, Gregg Neck Rd., Box 406, Galena, Md. 21635

[21] Appl. No.: 209,701

[22] Filed: Nov. 24, 1980

[51] Int. Cl.[3] ..... A01H 5/00

[52] U.S. Cl. ..... Plt./9

[58] Field of Search ..... Plt./9

*Primary Examiner*—Robert E. Bagwill
*Attorney, Agent, or Firm*—Vincent G. Gioia

[57] ABSTRACT

A new pink miniature rose which lightens upon aging.

1 Drawing Figure

The present invention relates to a new and distinct variety of rose plant of the miniature rose class, which was originated by my crossing as seed parent the rose known as "Rise 'N Shine" and the rose known as "Grand Opera" as pollen parent.

Among the novel characteristics possessed by this new variety which distinguish it from its parents and all other varieties of which I am aware are: (1) high centered flowers of unusual multi-pink tone coloring borne singly and in clusters, (2) relatively large blooms for this color range as compared to preexisting varieties and (3) an upright, well branched, vigorous plant. Asexual reproduction by budding of the new variety as performed in Kent County, Md., shows that the foregoing and other distinguishing characteristics come true to form and are established and transmitted through succeeding propagations.

The new and improved rose variety which I have developed is an unusual miniature rose in its coloring and size of blooms. Like many hybrid teas, the flowers are borne in clusters and singly. The changing pink tones combining Venetian Pink and French Rose colors upon aging result in an eye-catching plant for display with varying color tones often visible at the same time.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "36C" is plate 36C of the Royal Horticultural Society Color Chart.

Parentage: Seedling.
*Seed parent.*—"Rise 'N Shine".
*Pollen parent.*—"Grand Opera".
Class: Miniature.

The following observations are made of specimens grown under glass in Kent County, Md., during the month of March.

1. FLOWER

Blooming habit: Near continuous.

A. Bud:
(1) *Size.*—Small.
(2) *Form.*—Urn shaped.

(3) *Color.*—Petal undersurface first visible when sepals fall is off white varying from pale yellow cast at base (point of attachment) to 36C. Petal edge has deeper pink 50C color.
(4) *Sepals.*—Somewhat foliated, a little longer than bud, 144A.
(5) *Peduncle.*—Length — 3 to 4.5 cm. Aspect — straight. Strength — erect, strong. Color — 144A.

B. Bloom:
(1) *Size.*—Average size when fully expanded — about 4.5 cm.
(2) *Borne.*—Singly and in small clusters.
(3) *Form.*—High centered, becoming flat upon opening.
(4) *Petalage.*—Number of petals under normal conditions — about 65 to 70.
(5) *Color.*—As flowers mature sepals confine petals until about $\frac{1}{3}$ open, concentration of pink edges appears to give blooms darker pink centers 50C mixed with lighter tones; when flowers open further pink edges reflex and become less evident until at full open overall coloring is near 49D but with some deeper tone at petal edge. Between $\frac{1}{3}$ to full open coloring varies between 49B to 49C and then 49D. At full open yellowish stamens and pollen coloring are also visible.

C. Petals:
(1) *Texture.*—Relatively thick.
(2) *Appearance.*—Inside — satiny; outside — satiny.
(3) *Form.*—Tear shaped, reflexing to points on aging.
(4) *Arrangement.*—Shingle-like.
(5) *Petaloids in center.*—Few to none.
(6) *Persistence.*—Drop cleanly.
(7) *Fragrance.*—Very slight.
(8) *Lasting quality.*—Very long on plant and as cut flower (up to 3 weeks on bush, 7–10 days as cut flower).

2. REPRODUCTIVE ORGANS

A. Stamens, filaments and anthers:
(1) *Arrangement.*—Few anthers with normal stamens.
(2) *Color.*—16A.

B. Pollen:
*Color.*—164B.

C. Styles: Centered well but uneven.

D. Stigmas:
*Color.*—11C.

E. Hips: None observed.

3. PLANT

A. Form: Upright.

B. Growth: Very vigorous, uniform branching.
*Height attained.*—41 to 56 cm.

C. Foliage: Compound 5 to 7 leaflet leaves.
(1) *Size.*—Small to medium.
(2) *Quantity.*—Abundant.
(3) *Color.*—Upper side — 137A, new foliage with 187A edges. Under side — new 178A, old 138B.
(4) *Shape.*—Pointed, oval.
(5) *Texture.*—Upper side — flat. Under side — matte.
(6) *Edge.*—Serrated.
(7) *Serration.*—Regular, moderate (8–9 per cm.).
(8) *Leaf stem.*—Color — near to 146A. Under side — near to 145A.
(9) *Stipules.*—Medium length, slightly bearded.
(10) *Resistance to disease.*—Blackspot — none observed. Mildew — good.

D. Wood:
(1) *New wood.*—Color — near 147A. Bark — smooth.
(2) *Old wood.*—Color — near to 138A. Bark — smooth.

E. Thorns:
(1) *Thorns.*—Quantity — about 10 per 10 cm. On laterals from stalk — few. Form — thin, pointed, flat base. Length — short to medium. Color (when young) — 173A. Position — irregular.
(2) *Prickles.*—None.

F. Winter hardiness: Winter hardy.

I claim:

1. A new and distinct variety of rose plant of the miniature class, substantially as shown and described, characterized particularly by pink blooms showing darker pink edges borne until reflexing and lightening and with flowers of different pink tonality visible at the same time.

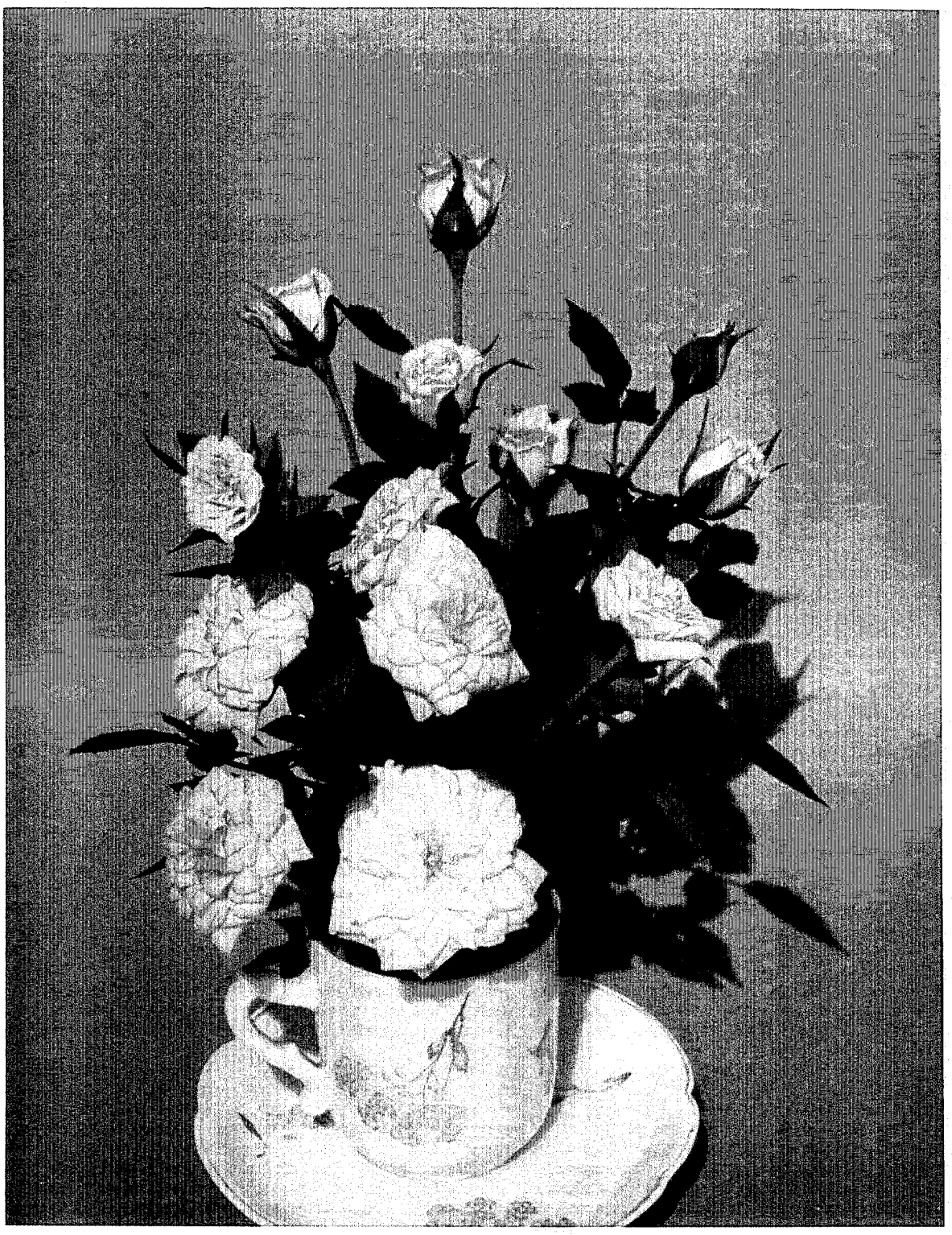

* * * * *